(12) United States Patent
Bauerfeind

(10) Patent No.: US 12,279,987 B2
(45) Date of Patent: Apr. 22, 2025

(54) PAD COMPRISING A PRESSURE ELEMENT

(71) Applicant: BAUERFEIND AG, Zeulenroda-Triebes (DE)

(72) Inventor: Hans B. Bauerfeind, Zeulenroda (DE)

(73) Assignee: BAUERFEIND AG, Zeulenroda-Triebes (DE)

( * ) Notice: Subject to any disclaimer, the term of this patent is extended or adjusted under 35 U.S.C. 154(b) by 639 days.

(21) Appl. No.: 17/637,740

(22) PCT Filed: Aug. 24, 2020

(86) PCT No.: PCT/EP2020/073613
§ 371 (c)(1),
(2) Date: Feb. 23, 2022

(87) PCT Pub. No.: WO2021/037789
PCT Pub. Date: Mar. 4, 2021

(65) Prior Publication Data
US 2022/0280329 A1   Sep. 8, 2022

(30) Foreign Application Priority Data
Aug. 26, 2019   (DE) .......................... 102019212740.1

(51) Int. Cl.
| | | |
|---|---|---|
| A61F 13/00 | (2024.01) | |
| A61F 5/00 | (2006.01) | |
| A61F 5/01 | (2006.01) | |
| A61F 5/30 | (2006.01) | |
| A61F 13/06 | (2006.01) | |

(52) U.S. Cl.
CPC .............. A61F 5/30 (2013.01); A61F 5/0106 (2013.01); A61F 13/06 (2013.01)

(58) Field of Classification Search
None
See application file for complete search history.

(56) References Cited

U.S. PATENT DOCUMENTS

| | | | |
|---|---|---|---|
| 9,545,328 B2 * | 1/2017 | Hess | ..................... A61F 13/061 |
| 9,943,434 B2 | 4/2018 | Jaeger et al. | |
| 2016/0324674 A1 | 11/2016 | Scheuermann et al. | |

FOREIGN PATENT DOCUMENTS

| | | | | |
|---|---|---|---|---|
| CN | 203749007 U | 8/2014 | | |
| CN | 204579954 U | 8/2015 | | |
| CN | 2493099 Y | 5/2022 | | |
| DE | 4103383 A1 | 8/1992 | | |
| DE | 102011010827 A1 * | 8/2012 | ........... | A61F 13/061 |
| DE | 102012021696 A1 * | 4/2014 | ........... | A43B 13/386 |
| DE | 102017108840 A1 | 10/2018 | | |

(Continued)

OTHER PUBLICATIONS

Translation of DE 102012021696 (Year: 2014).*

(Continued)

*Primary Examiner* — Kim M Lewis
(74) *Attorney, Agent, or Firm* — Dentons Durham Jones Pinegar; Sarah W. Matthews

(57) ABSTRACT

The invention relates to pads (200), in particular for orthopedic aids, comprising a pad pressure element (100, 101). The invention also relates to the use of the pads according to the invention in orthoses or bandages as well as to orthoses or bandages comprising pads according to the invention.

16 Claims, 7 Drawing Sheets

(56) References Cited

FOREIGN PATENT DOCUMENTS

JP      2002227440 A    8/2002
WO      2013191951 A1   12/2013

OTHER PUBLICATIONS

Translation of DE 102011010827 (Year: 2012).*
China National Intellectual Property Administration, "Notification of the First Office Action," Chinese Application No. 202080060532.8, Jun. 2, 2023.
China National Intellectual Property Administration, "Notification of the First Office Action," Chinese Application No. 202080060532.8, Jun. 2, 2023 (English translation only).
Korean Intellectual Property Office, "Office Action," for Korean Patent Application No. 10-2022-7006792, Oct. 30, 2024.
European Patent Office as International Searching Authority, "International Search Report and Written Opinion," International Application No. PCT/2020/073613, Nov. 24, 2020.

* cited by examiner

PAD COMPRISING A PRESSURE ELEMENT

CROSS-REFERENCE TO RELATED APPLICATIONS AND PRIORITY CLAIM

This application claims the benefit under 35 U.S.C. § 371 to International Application Number PCT/EP2020/073613 filed on Aug. 24, 2020, which claims the priority of German Patent Application No. 10 2019 212 740.1 filed on Aug. 26, 2019. The entire disclosures of said applications are incorporated by reference herein for all purposes and priority is claimed to said applications by the present application.

The invention relates to pads, in particular for orthopedic aids, comprising a pad pressure element. The invention also relates to the use of the pads according to the invention in orthoses or bandages as well as to orthoses or bandages comprising pads according to the invention.

Pads are known in various embodiments and for various prophylactic and therapeutic applications. Various pads are known, for example, from DE 27 22 563 C2, EP 0 598 291 A1, and EP 0 600 218 A2.

Pads made of two materials or components are also known from DE 297 01 001 U1. EP 0 496 071 A1 describes a pressure pad made of a softer material, in which at least one friction core made of a hard or incompressible material is arranged. This friction core is intended to provide a friction massage, that is to say a massage by movement-induced friction of painful points, which is generated by the movement of the core relative to the soft tissue of the pad carrier.

The pads from the prior art can exert pressure on the adjacent tissue in a planar manner or can distribute arising pressure across the surface and/or shield such pressure; however, these pads do not, or only insufficiently, allow a specific pressure, for example a stronger or weaker pressure, to be exerted on specific points.

In the case of pads from the prior art, the pressure is additionally applied perpendicularly to the skin. Lateral pressure, which in particular leads to a movement of the pressure elements, and thus brings about a massage effect that goes beyond simple pressure, is therefore not possible.

The technical problem underlying the present invention is therefore that of providing improved pads, in particular pads that, in addition to planar pressure, are able to exert specific, precise pressure. In particular, the technical problem underlying the present invention is that of providing a pad that leads to an improved massage effect, in particular a massage effect by the movement of the pressure body.

The technical problem underlying the invention is solved by providing a pad for orthopedic aids, comprising a pad base body made of a first material and at least one pad pressure element made of a second material, wherein the pad pressure element is at least partially embedded in the pad base body, and wherein the first material of the pad base body is softer than the second material of the pad pressure element, wherein the pad pressure element includes at least two pin-shaped elevations and a base element, wherein the pin-shaped elevations are arranged on the base element, and wherein the pin-shaped elevations can be moved in a viscoelastic manner by way of the base element.

The invention is therefore primarily characterized in that the at least two pin-shaped elevations are connected to one another above a base element and can be moved in a viscoelastic manner by way of the same when they are at least partially embedded in the pad base body.

The viscoelastic mobility of the pin-shaped elevations, in particular with respect to one another, can preferably be achieved by the flexible design of the base element. Therefore, the base element is preferably flexible.

The design of the pad according to the invention, comprising a novel pad pressure element made of pin-shaped elevations, which are connected by way of a base element and which are at least partially embedded in the softer pad base body and can be moved in a viscoelastic manner by way of the base element, advantageously results in an improved massage effect, in particular in a friction massage, in which not only pressure is exerted on the skin, but also a lateral movement takes place. It was found that, in the embodiment according to the invention, the pins connected to one another by way of the base element move toward one another or move away from one another, in particular at their ends lying furthest from the base element, when the pad is pressed perpendicularly onto the patient's skin. The movement of the pin-shaped elevations away from one another or toward one another advantageously represents a lateral movement, which is caused by the perpendicular pressure of the pad on the skin and which leads to an improved massage. In the process, it was advantageously found that this lateral movement takes place in a chaotic manner, which enhances the massage effect.

In comparison with elevations from the prior art, the pin-shaped elevations, which according to the invention are connected by way of the base element, that is to say particularly preferably also spoke-supported, spring back substantially more freely and movably, and thus in particular also more chaotically. This effect is advantageous, since the mechanoreceptors located directly beneath the skin surface have a more difficult time adjusting to the constantly slightly changing spring movement of the pin-shaped elevations. This leads to an extended action of the massage.

Since, in the case of manual therapy, massaging is "chaotic" because none of the therapist's movements are 100% identical, the massage action resulting from the pad according to the invention is more similar to that of a manual massage than the massage action by conventional pads. The connection of pin-shaped elevations, for example protuberance-like elevations, to base elements connected thereto, such as webs, which preferably also span holes in the base surface body in a spoke-like manner, advantageously results in movable elevations, which enable an intermittent massage principle. While immovable elevations on a pad only have a pressure effect which acts on the skin sensors, which, however, become accustomed to the pressure after a relatively short time and no longer emit effective signals, the movable pin-shaped elevations according to the invention lead to alternating pressure, such as that which, for example, a therapist exerts during a massage, so that the pressure action on lymphatic and blood vessels remains. This can, in particular, be advantageous in the case of a knee pad, for example, when a corresponding massage effect acts on the meniscus base and the Hoffa's fat pads. Surprisingly, it was additionally found that, when the pad pressure element is used without an enveloping component, the outer pin-like elements usually buckle inwardly when pressure is exerted on an inner pin-shaped element located on a web, while on the other hand, the outer pin-shaped elements, in the case of a pad pressure element according to the invention which is enveloped by a pad body, usually buckle outwardly when pressure is exerted on an inner pin-shaped element located on a web. Both effects are advantageous since they lead to a movement-induced massage similar to the manual massage.

While moving the pin-like elements apart from one another leads to a laterally directed pulling movement, the movement toward one another leads to a laterally directed pressure movement. Surprisingly, it has been found that this movement is also clearly transferred to the skin when the pin-shaped elements are at least partially embedded, for example potted, in the softer pad base body.

In the context of the present invention, a pad shall be understood to mean in particular a pressure pad, the shape of which is formed in particular by the pad base body. The pad base body can have any suitable shape. Conventional pads typically have planar base surfaces. Protrusions can then protrude from such a base surface. A pad according to the invention includes in particular a first base area or base surface which, when the pad is being used, faces the user. A pad is preferably configured to be substantially flat. Such a pad then preferably includes a second base area or base surface which faces away from the user when the pad is being used. The pin-shaped elevations point from the pad base body in the direction of the user.

The typical use of a pad is known to the person skilled in the art. Pads, including those according to the invention, are used in particular to exert pressure on certain body parts, for example in the region of the back or in the region of the kneecap. The pads are positioned in the process and pressed onto the corresponding body region using further devices, in particular bandages or orthoses.

In a preferred embodiment, at least a portion of the at least two pin-shaped elevations is embedded in the pad base body. Preferably, at least one of the at least two pin-shaped elevations is completely embedded in the pad base body. Preferably, the at least two pin-shaped elevations are completely embedded in the pad base body. Particularly preferably, the entire pad pressure element, that is to say the at least two pin-shaped elevations and the base element, is embedded in the pad base body, and the pad pressure element is thus preferably completely enclosed by the pad base body, for example potted into the pad base body.

The preferred complete sheathing of the at least one pad pressure element with the material of the pad base body not only results in the described application advantage, but also advantageously in a simpler manufacturing option of the pad according to the invention, since the second base surface of the pad base body, which faces away from the user, can thus be readily produced in a planar manner.

A pad is preferred, comprising a pad base body made of a material having a first hardness and at least one pad pressure element according to the invention made of a material having a second hardness, wherein the pad base body includes a first base surface facing the user and a second base surface facing away from the user, wherein the surface of the at least one pad pressure element is completely surrounded by the material of the pad base body.

The pad pressure element is preferably a pressure enhancement element. A pressure enhancement element is used to provide greater localized pressure than the surface pressure exerted by the pad base body.

In a preferred embodiment, the pad base body includes a first base surface facing the user and a second base surface facing away from the user, the pin-shaped elevations preferably projecting from the base element positioned in the region of the second base surface facing away from the user in the direction of the first base surface facing the user.

In a preferred embodiment, the at least two pin-shaped elevations protrude at least 2 mm into the pad base body.

In a preferred embodiment, the base element and the pin-shaped elevations are designed in one piece, and in particular they are made of the same material.

In a preferred embodiment, the base element of the pad pressure element is web-shaped or plate-shaped.

In a preferred embodiment, the base element has at least one hole, wherein the at least two pin-shaped elevations are preferably positioned on the base element at the edge of the at least one hole.

In a preferred embodiment, the at least two pin-shaped elevations are connected to one another by way of the web spanning the hole.

Preferably, the web is or the webs are assigned to the base element, or the web is or the webs are an integral part thereof.

In a preferred embodiment, at least two pairs of pin-shaped elevations are positioned at the edge of the hole and are in each case connected to one another by way of a web spanning the hole, wherein the webs of the two pairs of pin-shaped elevations intersect, preferably approximately in the center of the hole.

In a preferred embodiment, at least one further pin-shaped elevation is located on at least one web.

In a preferred embodiment, a further pin-shaped elevation is located on the intersecting point of the two webs.

As a result of the embodiment according to the invention, a specific pressure can advantageously be exerted in a targeted manner by the pin-shaped elevations on a certain tissue point. Such a specific tissue point can in particular be a trigger point.

If the webs preferably comprise additional pin-shaped elements, for example at the intersecting point of the webs, this leads to a further enhanced massage effect when these pin-shaped elevations located on the webs are pressed in and, as a result, the pin-shaped elevations located on the outside of the webs are moved in a manner mediated by the webs, in particular move away from the pin-shaped elevations located on the webs or move towards them. This movement leads to further massage effects.

The webs that are provided according to the invention and connect the pin-shaped elevations can also have differing widths and/or thicknesses. Depending on the thickness ratio or width ratio of the webs with respect to one another, the pin-shaped elevation connected by several webs, i.e. suspended, can deflect in a controlled manner. During spring deflection, the pin-shaped elevation is advantageously declined to the side on which the connecting web is weaker and/or thinner compared to the other webs.

In a preferred embodiment, the distance between adjacent pin-shaped elevations is at least 2.5 times and at most 6 times as wide as the height of the pin-shaped elevations. Particularly preferably, the distance between adjacent pin-shaped elevations is at least 3 times and at most 5 times as wide as the height of the pin-shaped elevations.

For example, approximately 3 mm high pin-shaped elevations are preferably spaced approximately 7.5 mm to 18 mm apart from one another, preferably 10 mm to 14 mm, and in particular approximately 12 mm.

In a preferred embodiment, the at least two pin-shaped elevations have the general shape of a pin, for example a pyramid, a cone, a cylinder, a hollow cylinder, a cuboid, a hexahedron, a prism, a polyhedron, a rod, a disk, a torus or a ring. The pin-shaped elevations can also be rod-shaped elevations.

The pin-shaped elevations have a first end, which is located at the base element and forms the pin foot, and a second end which forms the pin head. The pin head is thus the region of a pin-shaped elevation which is located the furthest away from the base element and which can thus be bent laterally the furthest.

The pin-shaped elevations point from the pad base body in the direction of the user, the pin head thus being situated in the direction of the first base surface of the pad base body, and the pin foot and the base element being situated in the direction of the second base surface of the pad base body.

The pin head can preferably bend laterally by at least 1 mm, particularly preferably by at least 2 mm, particularly preferably by at least 2.5 mm, wherein the bending can preferably take place in all directions. The bending path is measured from the pin foot, in particular from the center of the pin foot.

In a preferred embodiment, the at least two pin-shaped elevations have a height of at least 1 mm and at most 10 mm, for example of approximately 3 mm. In a preferred embodiment, the at least two pin-shaped elevations have a height of at least 2 mm. In a preferred embodiment, the at least two pin-shaped elevations have a height of at least 3 mm. The height is measured from the base element.

The pad is preferably at least partially viscoelastic, and thus preferably comprises at least one viscoelastic partial region. In particular, the pad is preferably at least viscoelastic in the region of the pad pressure element.

The pad base body preferably comprises a viscoelastic material at least in the region of the pad pressure element. Preferably, the pad base body is viscoelastic at least in a partial region. The pad base body is preferably viscoelastic. The pad base body is preferably made of a viscoelastic material.

The material of the pad base body is preferably plastic, silicone or rubber. However, a person skilled in the art is also familiar with further suitable materials for a pad base body from the prior art.

For example, the material can be thermoplastic elastomers. Polyurethanes are also suitable, for example.

The material of the pad base body is preferably bendable and/or expandable, so that the pad base body can adapt to the body shape of the user when the pad is applied.

The pad base body material is preferably not a textile material. In an alternative embodiment, however, the pad base body can also be surrounded by a textile sheath or be coated in another manner.

The pad base body material can, of course, also be made of mixtures of materials, in particular of at least two of the described materials.

The material of the pad pressure element is preferably a flexible material, in particular a flexible plastic material. In a preferred embodiment, the material of the at least one pad pressure element is plastic, silicone or rubber. Of course, the material of the at least one pad pressure element can also be made of mixtures of materials, in particular of at least two of the described materials.

The pin/base element design according to the invention can thus advantageously be easily produced, for example by means of injection molding technology.

According to the invention, the first material of the pad base body is softer than the second material of the pad pressure element.

In a preferred embodiment, the material of the pad base body has a Shore hardness of at least 10 Shore OO and at most 50 Shore OO.

The material of the pad base body, i.e., the first material, preferably has a hardness of at most 45 Shore OO, preferably at most 40 Shore OO, particularly preferably at most 30 Shore OO. The material of the pad base body, i.e., the first material, preferably has a hardness of at most 25 Shore OO, preferably at most 20 Shore OO, particularly preferably at most 19 Shore OO. The material of the pad base body preferably has a hardness of at least 10 Shore OO, in particular at least 14 Shore OO, particularly preferably at least 15 Shore OO.

In a preferred embodiment, the material of the pad pressure element has a Shore hardness of at least 10 Shore A, preferably at least 14 Shore A and at most 80 Shore A. In a preferred embodiment, the material of the pad pressure element has a Shore hardness of at least 20 Shore A and at most 80 Shore A.

In a preferred embodiment, the material of the at least one pad pressure element has a hardness of at least 20 Shore A and at most 60 Shore A.

In a preferred embodiment, the material of the at least one pad pressure element has a hardness of at least 20 Shore A, more preferably of at least 25 Shore A.

In a preferred embodiment, the material of the at least one pad pressure element has a hardness of at most 50 Shore A. In a preferred embodiment, the material of the at least one pad pressure element has a hardness of at most 49 Shore A, more preferably of at most 45 Shore A.

The material of the at least one pad pressure element preferably has a hardness of at least 35 to at most 45 Shore A. The material of the at least one pad pressure element preferably has a hardness of approximately 40 Shore A.

In a preferred embodiment, the material of the pad base body has a Shore hardness of at least 10 Shore OO and at most 50 Shore OO and/or the material of the pad pressure element has a Shore hardness of at least 10 Shore A, preferably at least 14 Shore A and at most 80 Shore A.

In a preferred embodiment, the pad comprises at least two flexible pad pressure elements, wherein the two pad pressure elements are connected to one another by way of a connecting element. Particularly preferably, the pad, in particular the knee pad, comprises four flexible pad pressure elements, wherein the four pad pressure elements are connected to one another by way of connecting elements.

The connecting elements which connect the pad pressure elements comprising at least two pin-shaped elevations to one another can preferably be web-shaped or plate-shaped.

Two pad pressure elements are preferred, each including two holes in the base element, in particular a first hole, at the edge of which at least two pairs of pin-shaped elevations are positioned, which are each connected to one another by way of a web spanning the hole, wherein the webs of the two pairs of pin-shaped elevations intersect one another, preferably approximately in the center of the hole, and a second hole, at the edge of which at least one pair of pin-shaped elevations is positioned, which is connected to one another by way of a first web spanning the hole, wherein a second web spans the hole, wherein the first and second webs intersect one another, preferably approximately in the center of the hole, wherein the two pad pressure elements are connected to one another by way of a connecting element.

Preferred are two pad pressure elements, each comprising a flexible base element, in each case including two holes, having pin-shaped elevations and webs, wherein the pad pressure elements are connected to one another by way of a connecting element, as is shown in FIG. 3.

Preferably, the two or more pad pressure elements and the connecting element are produced in one piece and/or from the same material.

The pad, in particular the part of the pad base body formed by the first base surface and the second base surface, can have any shape, in particular any pad shape known to a person skilled in the art.

For example, the pad can be annular, in particular when it is used as a patella pad. Alternatively, the shape can also be a flat continuous surface. Wing-shaped appendages can be provided on one or more sides of the pads.

The pad is preferably a knee pad, an ankle pad, a back pad, an elbow pad, a pad for the arm region or a pad for the abdominal region.

In a preferred embodiment, the pad comprises at least two pad pressure elements. In a preferred embodiment, the pad comprises at least two to at most twenty pad pressure elements. In a preferred embodiment, the pad comprises a plurality of pad pressure elements.

The plurality of pad pressure elements can be positioned on the first base surface of the pad in such a way that, when the pad is used, they exert the precise pressure on specific points, for example on trigger points, on acupuncture points or on infrapatellar fat pads.

In an alternative embodiment, the at least two pad pressure elements, in particular a plurality of pad pressure elements, can also be connected to one another by way of webs in the pad base body.

In addition to the at least one pad pressure element, the pad can also additionally comprise friction elements, for example made of the pad base body material.

In a preferred embodiment, the pad is a knee pad, an ankle pad, a back pad, an elbow pad, a pad for the arm region or a pad for the abdominal region. In a preferred embodiment, the pad is a knee pad, an ankle pad, an elbow pad, a pad for the arm region or a pad for the abdominal region. In a preferred embodiment, the pad is a knee pad, an ankle pad, an elbow pad or a pad for the arm region. In a particularly preferred embodiment, the pad is a knee pad.

In a preferred embodiment, the pad is a knee pad and comprises at least two pad pressure elements, wherein the two pad pressure elements of the pad are positioned in the pad base body so that they are located in the region of the infrapatellar fat pad when the pad is applied and can exert pressure thereon.

A pad is preferred, wherein the at least one pad pressure element of the pad is positioned in the pad base body so as to be located in the region of a trigger point when the pad is applied and can exert pressure on the trigger point.

A pad according to the invention is preferably used in trigger point therapy, wherein the at least one pad pressure element of the pad is preferably positioned in the pad base body so as to press on a trigger point when the pad is worn.

The trigger point therapy has the goal of eliminating so-called myofascial trigger points. These are locally delimited hardened areas in the skeletal muscle.

A pad, in particular a knee pad, as shown in FIGS. 5 and 6 is preferred.

The pad according to the invention is preferably not a pad for the back. The pad according to the invention is preferably not a back pad.

The pad according to the invention is preferably not a shoe insert or foot insole.

The pad is preferably for an orthopedic aid. The pad is preferably an integral part of an orthopedic aid. The orthopedic aid can be an orthosis or a bandage.

The present invention also relates to an orthopedic aid comprising a pad according to the invention. The present invention also relates to an orthosis or a bandage comprising a pad according to the invention.

In a preferred embodiment, the orthosis or bandage is a knee orthosis or knee bandage, an ankle orthosis or bandage, a back orthosis or bandage, an elbow orthosis or bandage, an orthosis or bandage for the arm region or an orthosis or bandage for the abdominal region. In a preferred embodiment, the orthosis or bandage is a knee orthosis or knee bandage, an ankle orthosis or bandage, an elbow orthosis or bandage, an orthosis or bandage for the arm region or an orthosis or bandage for the abdominal region. In a preferred embodiment, the orthosis or bandage is a knee orthosis or knee bandage, an ankle orthosis or bandage, an elbow orthosis or bandage, or an orthosis or bandage for the arm region.

In a preferred embodiment, the orthosis or bandage is a knee orthosis or knee bandage.

Preferably, the orthosis is an elastic knitted orthosis or the bandage is an elastic knitted bandage, in particular a knee bandage.

In a preferred embodiment, the orthosis or bandage is not a back orthosis or back bandage.

The present invention also relates to the use of a pad according to the invention as a pressure pad, preferably in bigger point therapy.

The present invention also relates to a method for trigger point therapy, in which a pad according to the invention is applied to a user in a first step in such a way that the at least one pad pressure element presses onto a trigger point, and in a second step the pad according to the invention is worn in this position by the user over a certain period of time.

Further preferred subjects of the invention will become apparent from the dependent claims and the independent claims.

The invention is described in more detail based on the following figures, without the embodiments of the invention shown therein being understood as limiting.

Figure 1:
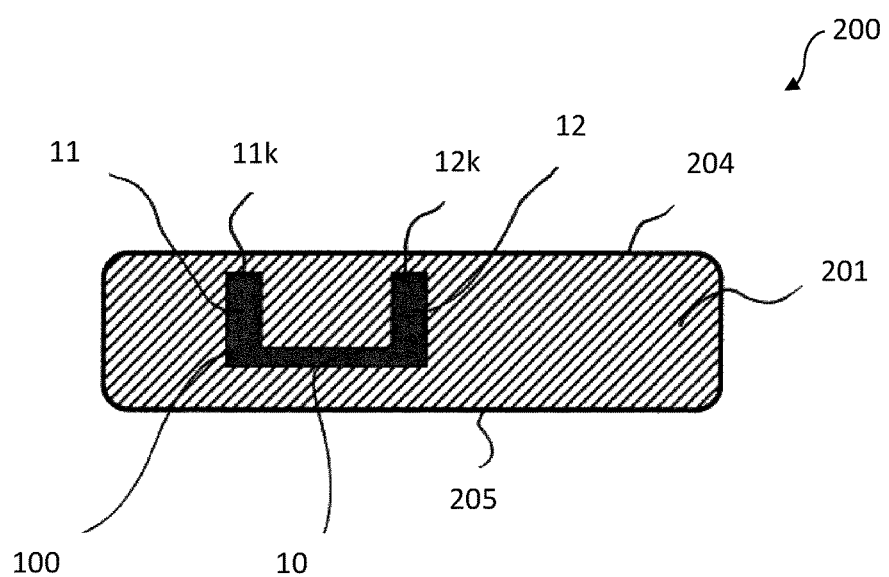
FIG. 1 shows the basic design of a pad according to the invention.

FIG. 1 shows a pad (200) according to the invention, which comprises a pad base body (201) in which a pad pressure element (100) is embedded. The pad pressure element (100) is designed in one piece and made of a flexible material which is harder than the material of the pad base body (201). The pad (200) has a first side including a first base surface (204) and an opposite second side including a second base surface (205). When the pad (200) is in use, the first base surface (204) is directed in the direction of the user, that is, it is pressed onto the skin of the user, wherein, of course, an intermediate layer can also be situated between the pad (200) and the skin, for example a cladding layer made of fabric.

The pad pressure element (100) includes a first pin-shaped elevation (11) and a second pin-shaped elevation (12), wherein the two pin-shaped elevations (11, 12) are connected to one another at the pin feet thereof by way of a flexible base element (10). The base element (10) is positioned in the pad base body (201) in the direction of the second base surface (205), while the pin-shaped elevations run in the direction of the first base surface (204), in the vicinity of which the pin heads (11k, 12k) are thus located.

If the pad (200) is now pressed onto the skin of the user, for example by means of a bandage, the pin-shaped elevations (11, 12) move toward or away from one another, in particular in the region of the heads (11k, 12k) thereof. The perpendicular pressure thus results in a lateral movement of the pin-shaped elevations (11, 12). This sideways movement of the pin-shaped elevations (11, 12) results in an improved massage effect, which significantly exceeds a simple vertical pressure of the pin heads (11k, 12k) on the skin of the user. The different pressure influences during the movement of the user result in a chaotic sideways movement of the pin-shaped elevations (11, 12), which imitates the chaotic movement during a manual massage.

Figure 2:
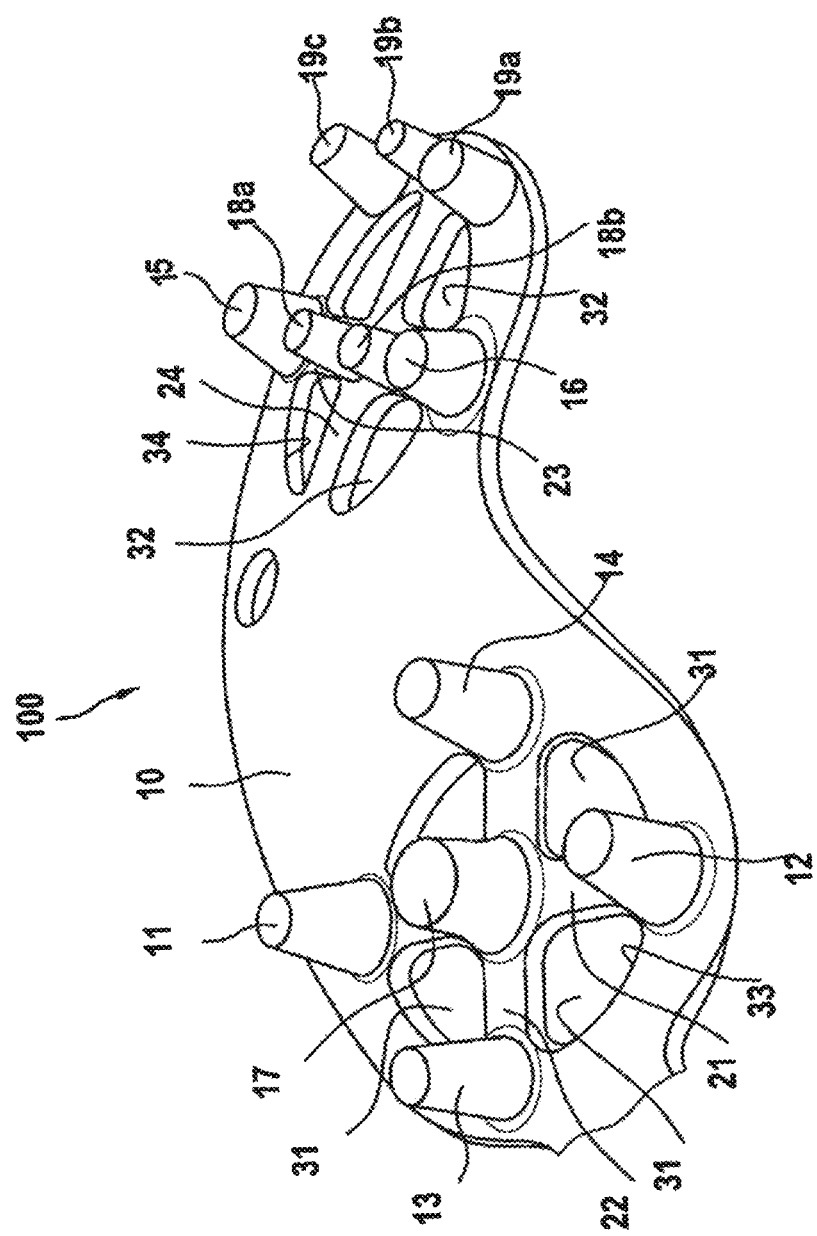
FIG. 2 shows a preferred embodiment of a pad pressure element of a pad according to the invention.

FIG. 2 shows a preferred embodiment of a pad pressure element (100) of a pad according to the invention, here a knee pad. The pad pressure element (100) comprises a flexible base element (10) including two holes (31, 32). In the case of the first hole (31), four pin-shaped elevations (11, 12, 13, 14) are arranged at the hole edge (33). The four pin-shaped elevations form a first opposing pair (11, 12) and a second opposing pair (13, 14). The first pair of pin-shaped elevations (11, 12) is connected to one another by way of a first web (21). The second pair of pin-shaped elevations (13, 14) is also connected to one another by way of a second web (22). The two webs (21, 22) intersect in the center of the hole (31). At the intersecting point of the webs (21, 22), a further central pin-shaped elevation (17) is situated. The flexible base surface body (10) includes a second hole (32), two opposing pin-shaped elevations (15, 16) being located at the hole edge (34) of the second hole (32), which are likewise connected to one another by way of a web (23) which spans the hole (32). This web (23) includes two further, central pin-shaped elevations (18a, 18b). The first web (23) is intersected by a second web (24), which also spans the hole (32) and which starts in the region of three further rod-shaped elevations (19a, 19b, 19c) at the base element (10) which are located at the hole edge (34).

The pad pressure element (100) is molded from a single flexible plastic material by injection molding.

Figure 3:
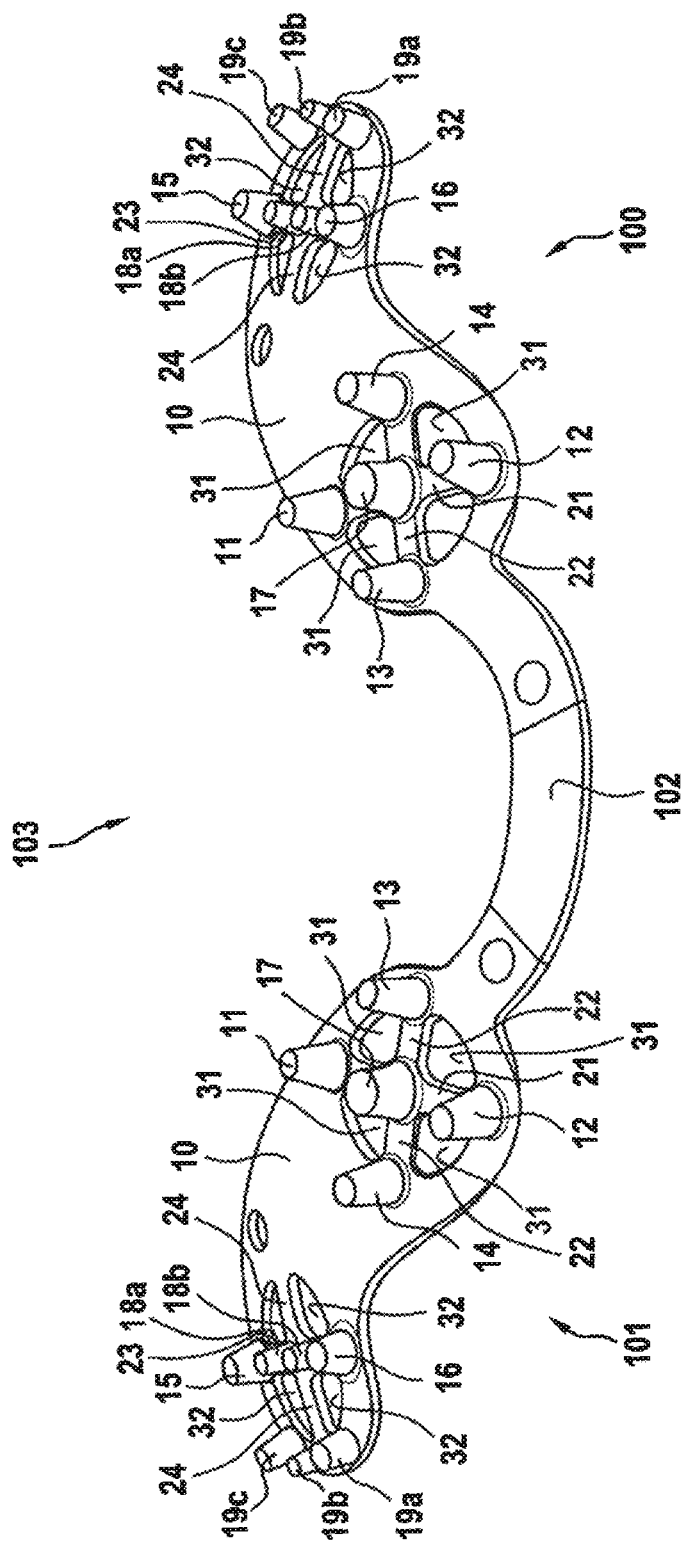
FIG. 3 shows a preferred embodiment of two pad pressure elements of a pad according to the invention connected to one another.

FIG. 3 shows a preferred embodiment of two pad pressure elements (100, 101) of a pad according to the invention, which are connected to one another by way of a connecting element (102) and thus form a unit (103). The pad pressure element (100) corresponds to the pad pressure element from FIG. 2. Again, the pin-shaped elevations (11, 12, 13, 14, 15, 16, 17, 18a, 18b, 19a, 19b, 19c) are shown, which are situated in the region of the two holes (31, 32), as well as the webs (21, 22, 23, 24) spanning the holes. The base element (10) is connected by way of a connecting element (102) to the base element (10) of the second pad pressure element (101). The second pad pressure element (101) is shown mirror-inverted to the first pad pressure element (100), but again shows the pin-shaped elevations (11, 12, 13, 14, 15, 16, 17, 18a, 18b, 19a, 19b, 19c), which are positioned in the region of the two holes (31, 32), the holes being spanned by the webs (21, 22, 24). Such a unit (103) of two pad pressure elements (100, 101) is suitable in particular for use in a knee pad of a knee bandage.

Figure 4:
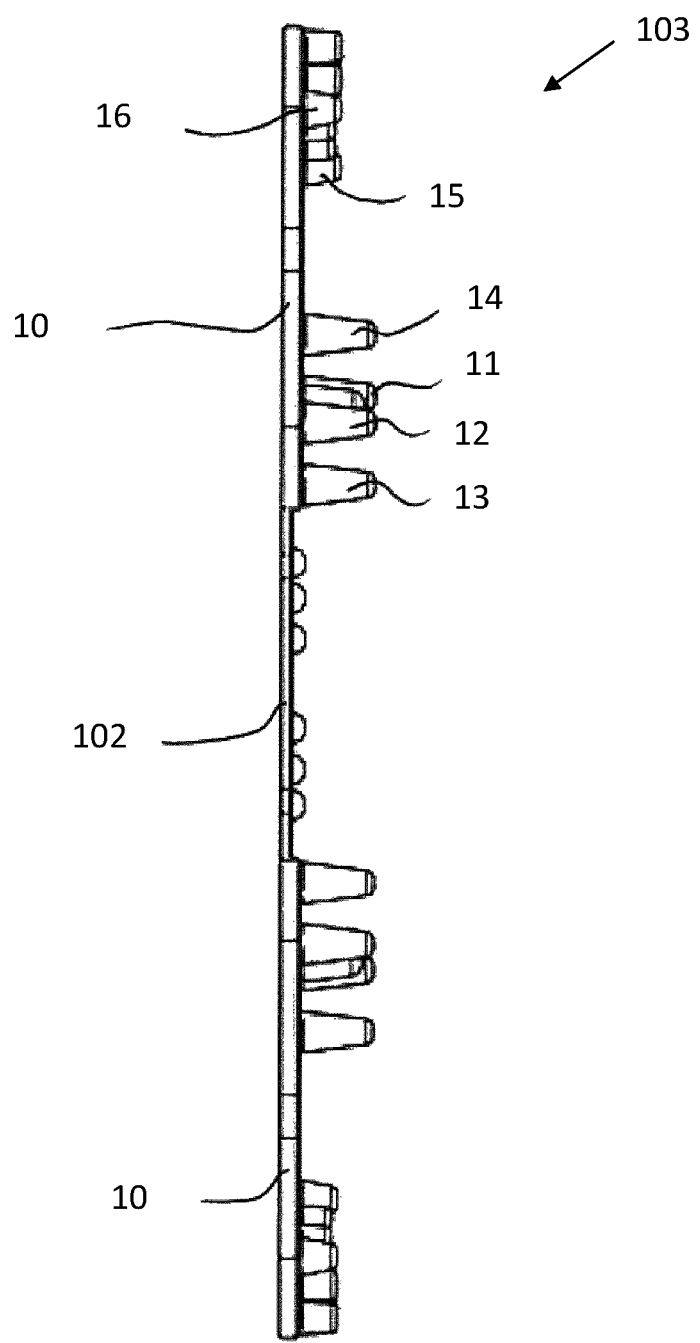
FIG. 4 shows a side view of the two pad pressure elements from FIG. 3 connected to one another.

FIG. 4 shows the pad pressure element unit (103) from FIG. 3 in a side view. The two base elements (10) can be seen, which are connected to one another by way of the connecting element (102). The pin-shaped elevations (11, 12, 13, 14, 15, 16) shown in FIG. 3 protrude from the base elements (10).

Figure 5:
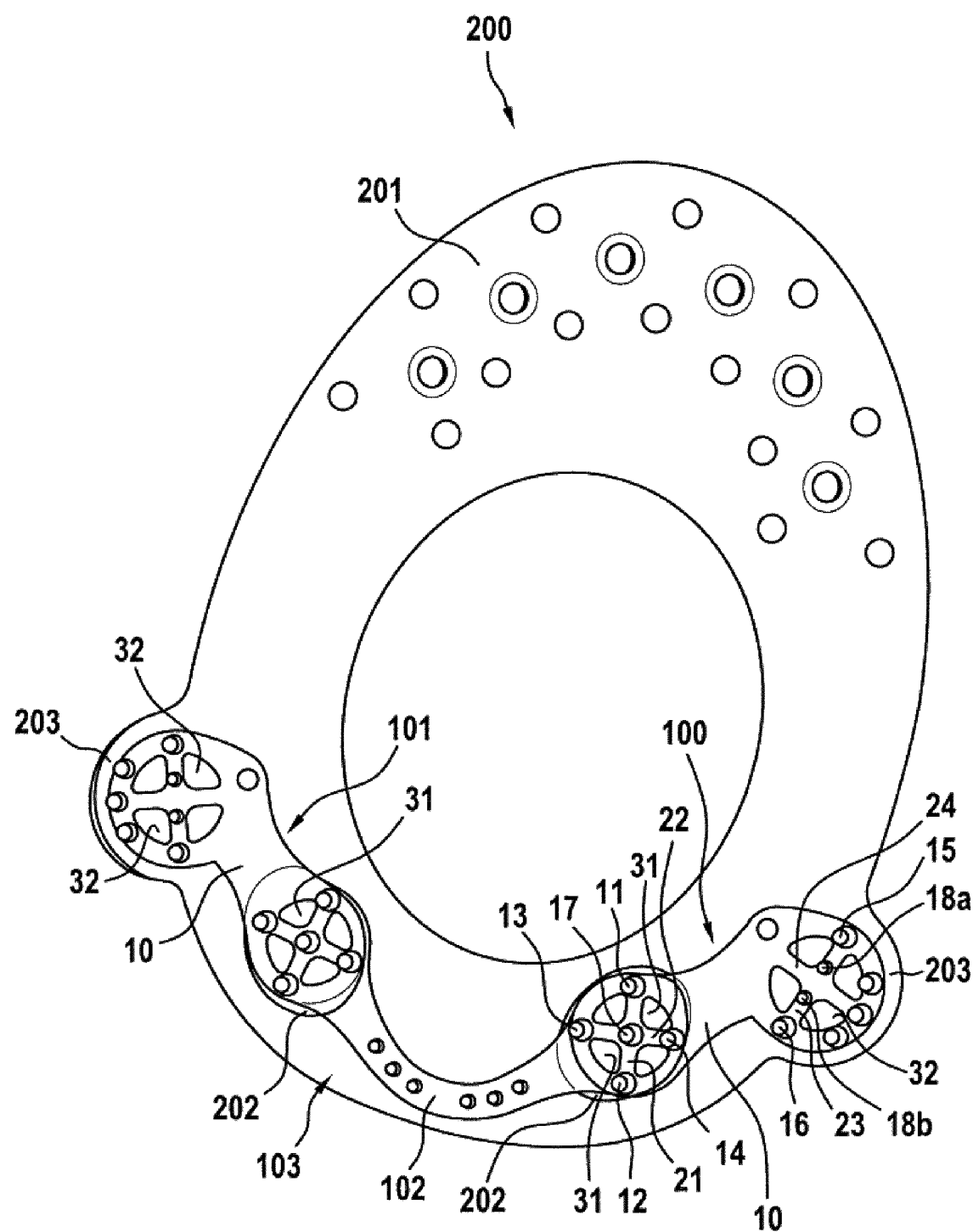
FIG. 5 shows a pad according to the invention comprising the pad pressure elements from FIG. 3.

FIG. 5 shows a knee pad (200) comprising an annular pad base body (201). The pad base body (201) comprises two protuberance-shaped protrusions (202) and two wing-shaped protrusions (203) as are known, for example, from DE 10 2011 010 827 A1 and fulfill the function described therein, that is to say, they are located in the region of the infrapatellar fat pads and can exert pressure thereon or can become engaged with the infrapatellar joint space. The plan view onto the pad (200) is shown, so that the first surface of the pad facing the user can be seen. The unit (103) from FIG. 3 made up of the two pad pressure elements (100, 101), which are connected to one another by way of a connecting element (102), is completely embedded in the pad base body (201), and more particularly in such a way that the flexible base element (10) is in each case positioned such that the first holes (31) including the associated pin-shaped elevations (11, 12, 13, 14, 17) and webs (21, 22) are situated in the protuberance-shaped protrusions (202), and the second holes (32) including the associated pin-shaped elevations (15, 16, 18a, 18b) and the webs (23, 24) are positioned in the region of the wing-shaped protrusions (203).

The massage effects caused by the design according to the invention can thus act on the important regions below and next to the kneecap.

Figure 6:
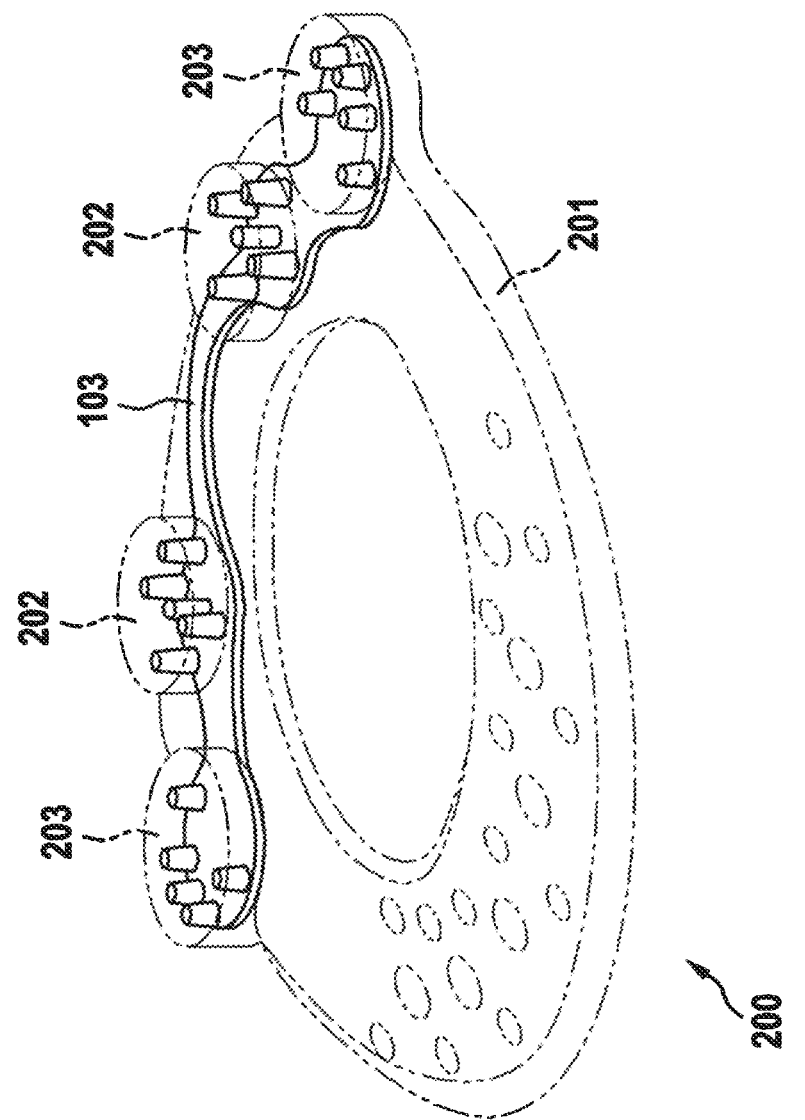
FIG. 6 shows the pad according to the invention from FIG. 5 in an oblique view.

FIG. 6 shows the knee pad (200) from FIG. 5 in an oblique view. The unit (103) made up of the two pad pressure elements and the connecting element is integral and completely potted into the pad base body (201). The different pin-shaped elevations are situated in the region of the protuberance-shaped protrusions (202) and the wing-shaped protrusions (203) the pad base body (201). As a result, both a pressure and a massage action are advantageously exerted in the region of the infrapatellar fat pads.

Figure 7:
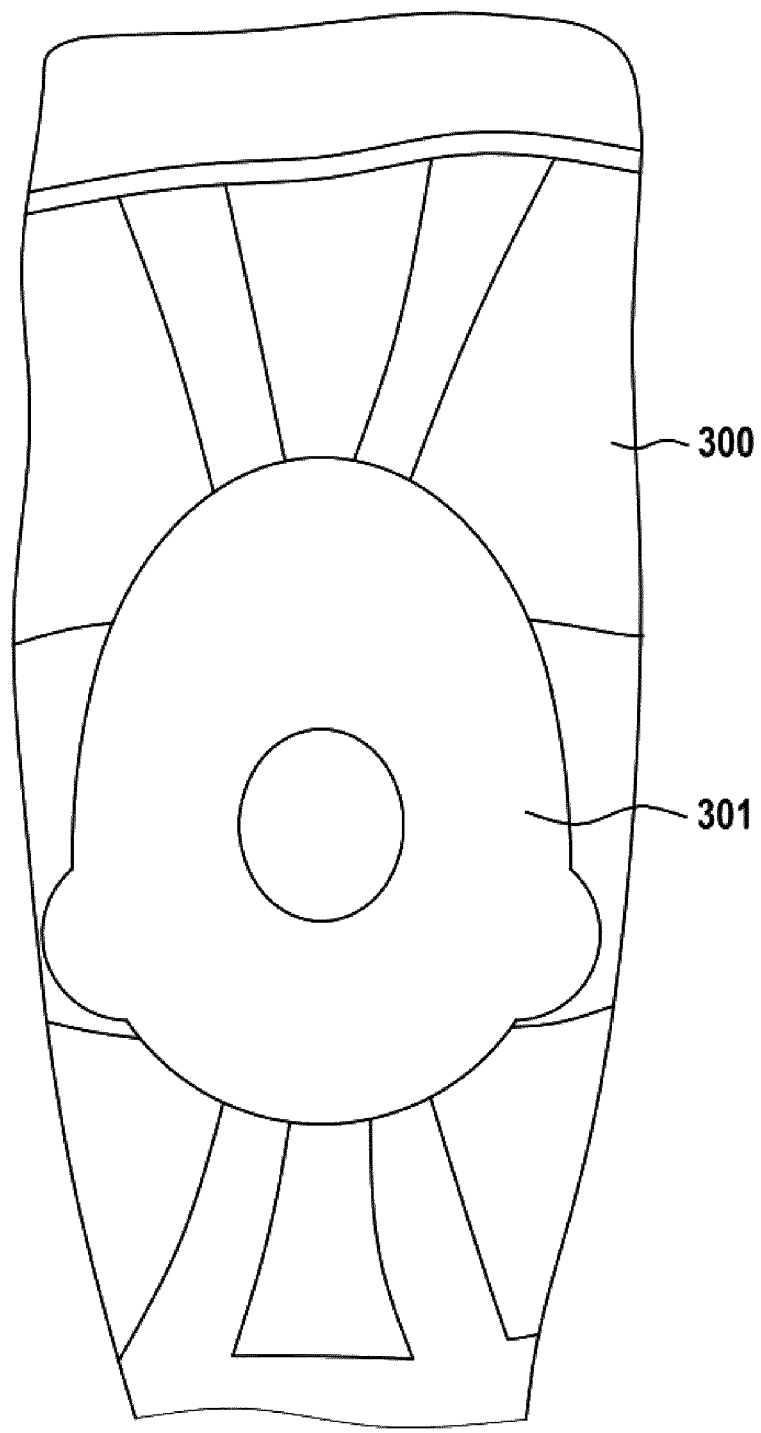
FIG. 7 shows the inner side of a knitted knee bandage comprising a pad according to the invention.

FIG. 7 shows a knee bandage (300) according to the invention, which is made of a knitted fabric and comprises a pad according to the invention. The inside of the bandage (300) can be seen here. The pad rests on the inside of the knitted bandage fabric and is positioned and attached there by way of a cladding material (301) so that only the contour of the pad can be seen in the figure. When the knee bandage (300) is worn, the pad is located in the region of the knee and surrounds the kneecap, so that the wing-shaped protrusions and protuberance-shaped protrusions end up in the region of the infrapatellar fat pads, and the pad is able to act there with the pin-shaped elevations.

LIST OF REFERENCE SIGNS

10 Base element
11 Pin-shaped elevation
11k Pin head
12 Pin-shaped elevation
12k Pin head
13 Pin-shaped elevation
14 Pin-shaped elevation
15 Pin-shaped elevation
16 Pin-shaped elevation
17 Pin-shaped elevation
18a Pin-shaped elevation
18b Pin-shaped elevation
19a Pin-shaped elevation
19b Pin-shaped elevation
19c Pin-shaped elevation
21 First web
22 Second web
23 Web
24 Web
31 Hole
32 Hole
33 Hole edge 34 Hole edge
100 Pad pressure element
101 Pad pressure element
102 Connecting element
103 Two pad pressure elements connected to one another by way of a connecting element
200 Pad
201 Pad base body
202 Protuberance-shaped protrusions
203 Wing-shaped protrusions
204 First base surface
205 Second base surface
300 Knitted bandage
301 Cladding material

The invention claimed is:

1. A pad for orthopedic aids, comprising a pad base body made of a first material and at least one pad pressure element made of a second material, the pad pressure element being at least partially embedded in the pad base body, and the first material of the pad base body being softer than the second material of the pad pressure element, the pad pressure element comprising at least two pin-shaped elevations and a base element, the pin-shaped elevations being arranged on the base element, the pin-shaped elevations being movable in a viscoelastic manner by way of the base element, the base element including at least one hole, and the at least two pin-shaped elevations on the base element being positioned at an edge of the at least one hole, characterized in that the at least two pin-shaped elevations are connected to one another by way of a web spanning the hole, and at least one further pin-shaped elevation being located on the web.

2. The pad according to claim 1, characterized in that at least a portion of the at least two pin-shaped elevations is embedded in the pad base body.

3. The pad according to claim 1, characterized in that the base element of the pad pressure element is web-shaped or plate-shaped.

4. The pad according to claim 1, characterized in that the pad comprises at least two flexible pad pressure elements, the two pad pressure elements being connected to one another by way of a connecting element.

5. The pad according to claim 1, characterized in that the at least two pin-shaped elevations protrude at least 2 mm into the pad base body.

6. The pad according to claim 1, characterized in that at least two pairs of pin-shaped elevations are positioned at the edge of the hole and are in each case connected to one another by way of a web spanning the hole, the webs of the two pairs of pin-shaped elevations intersecting, approximately in the center of the hole.

7. The pad according to claim 6, characterized in that a further pin-shaped elevation is arranged on and/or-next to the intersecting point of the twe webs.

8. The pad according to claim 1, characterized in that the base element and the pin-shaped elevations are designed in one piece, and in particular made of the same material.

9. The pad according to claim 1, characterized in that the pad base body includes a first base surface facing a user and a second base surface facing away from the user, the pin-shaped elevations projecting from the base element positioned in the second base surface facing away from the user in the direction of the first base surface facing the user.

10. The pad according to claim 1, characterized in that the material of the pad base body has a Shore hardness of at least 10 Shore OO and at most 50 Shore OO and the material of the pad pressure element has a Shore hardness of at least 10 Shore A and at most 80 Shore A.

11. The pad according to claim 1, characterized in that a distance between adjacent pin-shaped elevations is at least 2.5 times and at most 6 times as wide as a height of the pin-shaped elevations.

12. The pad according to claim 1, characterized in that the pad is a knee pad, an ankle pad, a back pad, an elbow pad, a pad for the arm region or a pad for the abdominal region.

13. The pad according to claim 1, characterized in that the pad is a knee pad and comprises at least two pad elements, the two pad elements of the pad being positioned in the pad base body so that they are located in a region of the user's infrapatellar fat pads when the pad is applied and can exert pressure thereon.

14. An orthosis or a bandage comprising a pad according to claim 1.

15. The pad according to claim 6, characterized in that a further pin-shaped elevation is arranged on or next to the intersecting point of the webs.

16. The pad according to claim 1, characterized in that the material of the pad base body has a Shore hardness of at least 10 Shore OO and at most 50 Shore OO or the material of the pad pressure element has a Shore hardness of at least 10 Shore A and at most 80 Shore A.

* * * * *